US011471619B2

(12) United States Patent
Garcia et al.

(10) Patent No.: US 11,471,619 B2
(45) Date of Patent: Oct. 18, 2022

(54) EREPTIOSPIRATION DEVICE FOR MEDICINAL WAXES, SOLIDS, BIOPOLYMERS, OR HIGHLY VISCOUS OILS, AND CANNABINOIDS

(71) Applicant: Arizona Board of Regents on Behalf of Arizona State University, Scottsdale, AZ (US)

(72) Inventors: Antonio Garcia, Chandler, AZ (US); Christine Woolley, Phoenix, AZ (US); Marco Santello, Gilbert, AZ (US)

(73) Assignee: ARIZONA BOARD OF REGENTS ON BEHALF OF ARIZONA STATE UNIVERSITY, Scottsdale, AZ (US)

( * ) Notice: Subject to any disclaimer, the term of this patent is extended or adjusted under 35 U.S.C. 154(b) by 312 days.

(21) Appl. No.: 16/069,461

(22) PCT Filed: Jan. 11, 2017

(86) PCT No.: PCT/US2017/013046
§ 371 (c)(1),
(2) Date: Jul. 11, 2018

(87) PCT Pub. No.: WO2017/123654
PCT Pub. Date: Jul. 20, 2017

(65) Prior Publication Data

US 2019/0022338 A1 Jan. 24, 2019

Related U.S. Application Data

(60) Provisional application No. 62/277,083, filed on Jan. 11, 2016.

(51) Int. Cl.

| | |
|---|---|
| ***A61M 11/04*** | (2006.01) |
| ***A61M 15/06*** | (2006.01) |
| ***H05B 1/02*** | (2006.01) |

(52) U.S. Cl.
CPC .......... *A61M 11/042* (2014.02); *A61M 15/06* (2013.01); *H05B 1/0227* (2013.01); *A61M 2205/8206* (2013.01)

(58) Field of Classification Search
CPC ................ A61M 15/06; A61M 11/042; A61M 2205/8206; H05B 1/0227
(Continued)

(56) References Cited

U.S. PATENT DOCUMENTS 1,775,947 A * 9/1930 Robinson .............. A61M 15/00
128/203.27
3,668,224 A * 6/1972 Petrzilka .............. C07D 311/80
549/390
(Continued)

FOREIGN PATENT DOCUMENTS

CN 105072934 11/2015
EP 2875740 B1 5/2016
(Continued)

OTHER PUBLICATIONS

International Search Report and Written Opinion for International Patent Application No. PCT/US2017/013046 dated Mar. 13, 2017.
(Continued)

*Primary Examiner* — Eric S Stapleton
(74) *Attorney, Agent, or Firm* — Quarles & Brady, LLP

(57) ABSTRACT

Provided herein is a device for ereptiospirating an inhalable material such as a medical wax or solid or highly viscous oil comprising a medication. More particularly, provided herein is a device for continuously ereptiospirating an inhalable material and for delivery of dosages of the inhalable material to patients via direct lung inhalation.

13 Claims, 6 Drawing Sheets

(58) Field of Classification Search
USPC .......................................................... 392/386
See application file for complete search history.

(56) References Cited

U.S. PATENT DOCUMENTS

| | | | | | |
|---|---|---|---|---|---|
| 5,249,586 | A * | 10/1993 | Morgan | A24B 15/14 131/194 |
| 5,499,636 | A * | 3/1996 | Baggett, Jr. | A24F 47/008 131/194 |
| 5,564,442 | A * | 10/1996 | MacDonald | A24F 13/00 131/194 |
| 5,692,525 | A * | 12/1997 | Counts | A24F 47/008 131/194 |
| 5,692,526 | A * | 12/1997 | Adams | A24F 47/008 131/194 |
| 6,026,820 | A * | 2/2000 | Baggett, Jr. | A24F 47/008 131/370 |
| 8,402,976 | B2 * | 3/2013 | Fernando | A24F 47/00 131/194 |
| 8,558,147 | B2 * | 10/2013 | Greim | A24F 47/008 219/507 |
| 8,833,364 | B2 * | 9/2014 | Buchberger | A61M 11/041 128/202.21 |
| 9,016,274 | B1 * | 4/2015 | White | A61M 15/00 128/202.21 |
| 9,084,440 | B2 * | 7/2015 | Zuber | A24F 47/008 |
| 9,439,454 | B2 * | 9/2016 | Fernando | A24F 47/008 |
| 9,995,688 | B2 * | 6/2018 | Garcia | G01N 21/49 |
| 2006/0032501 | A1 * | 2/2006 | Hale | A61M 11/041 128/203.12 |
| 2006/0102175 | A1 * | 5/2006 | Nelson | A61M 11/042 128/200.24 |
| 2006/0147520 | A1 * | 7/2006 | Ruegg | A61K 9/1617 424/464 |
| 2008/0044472 | A1 * | 2/2008 | Garcia | A61P 29/00 424/484 |
| 2009/0078326 | A1 * | 3/2009 | Rosario | B01L 3/502746 137/827 |
| 2009/0180968 | A1 * | 7/2009 | Hale | A61K 31/573 424/40 |
| 2010/0006092 | A1 * | 1/2010 | Hale | A61M 15/0031 128/202.21 |
| 2011/0126848 | A1 * | 6/2011 | Zuber | A24F 47/008 131/329 |
| 2011/0147486 | A1 * | 6/2011 | Greim | H05B 3/18 239/135 |
| 2011/0226236 | A1 * | 9/2011 | Buchberger | A61M 15/0086 128/200.23 |
| 2012/0269497 | A1 * | 10/2012 | Hatten | A61M 11/042 392/386 |
| 2013/0152922 | A1 * | 6/2013 | Benassayag | A61M 11/042 128/202.21 |
| 2013/0220315 | A1 * | 8/2013 | Conley | H05B 1/0244 128/202.21 |
| 2013/0247910 | A1 * | 9/2013 | Postma | A61M 15/06 128/203.26 |
| 2014/0041655 | A1 * | 2/2014 | Barron | A61M 15/06 128/202.21 |
| 2014/0069424 | A1 * | 3/2014 | Poston | A61M 11/042 128/202.21 |
| 2014/0166027 | A1 * | 6/2014 | Fuisz | A61K 31/352 131/328 |
| 2014/0205272 | A1 * | 7/2014 | Midgette | A01M 1/2077 392/395 |
| 2014/0228519 | A1 * | 8/2014 | Nakayama | C08L 63/04 525/109 |
| 2014/0251355 | A1 * | 9/2014 | Tracey | A24F 1/30 131/328 |
| 2014/0305454 | A1 * | 10/2014 | Rinker | H05B 3/26 131/329 |
| 2015/0069047 | A1 * | 3/2015 | Greim | H05B 1/0244 219/539 |
| 2015/0105455 | A1 * | 4/2015 | Bjorncrantz | A61K 31/05 514/454 |
| 2015/0136158 | A1 * | 5/2015 | Stevens | A61M 15/06 131/329 |
| 2015/0182455 | A1 * | 7/2015 | Llamas | A61K 31/352 514/729 |
| 2015/0196060 | A1 * | 7/2015 | Wensley | A61M 11/042 392/390 |
| 2015/0328415 | A1 * | 11/2015 | Minskoff | A61M 15/06 128/202.21 |

FOREIGN PATENT DOCUMENTS

| | | | |
|---|---|---|---|
| WO | 2005072334 | A2 | 8/2005 |
| WO | 2006014930 | A2 | 2/2006 |
| WO | 2006017892 | A1 | 2/2006 |
| WO | 2006132640 | A2 | 12/2006 |
| WO | 2011034678 | A1 | 3/2011 |
| WO | 2015073854 | A2 | 5/2015 |
| WO | 2019014373 | A1 | 1/2019 |

OTHER PUBLICATIONS

Ahrenberg, Mathias, et al. "Determination of volatility of ionic liquids at the nanoscale by means of ultra-fast scanning calorimetry." Physical Chemistry Chemical Physics 16.7 (2014): 2971-2980.

Alexza Pharmaceuticals, Staccato Platform Details, available on the internet, http://alexza.com/staccato/staccato-overview (2016).

Burstein, Sumner H., et al. "Synthetic nonpsychotropic cannabinoids with potent antiinflammatory, analgesic, and eukocyte antiadhesion activities." Journal of medicinal chemistry 35.17 (1992): 3135-3141.

Cebe, Peggy, et al. "Beating the heat-fast scanning melts silk beta sheet crystals." Scientific reports 3 (2013): 1130.

Große, W., The mechanism of thermal transpiration (=thermal osmosis). Aquatic Botany, 1996, 54 (2-3), 101-110.

Gupta N.K. et al., A high-flow Knudsen pump using a polymer membrane: performance at and below atmospheric pressures. Micro Electro Mechanical Systems (MEMS), 2010 IEEE 23rd International Conference.

Howard, W.M., An Experimental Investigation of Pressure Gradients due to Temperature Gradients in Small Diameter Tubes, Thesis, California Institute of Technology 1955.

Jacobs Online. Heat Transfer coefficient of 200 W/m2-K is reasonable for natural convection and the following online calculator for Nichrome wire temperature uses this value http://www.jacobs-online.biz/nichrome/NichromeCalc.html.

Kamble, R.M., et al, Stability-indicating RP-HPLC method for analysis of paracetamol and tramadol in a pharmaceutical dosage form, E-Journal of Chemistry 2012, 9(3), 1347-1356.

Kanthal. Thermal and mechanical properties found on the internet at http://www.kanthal.com/en/products/material-datasheets/wire/resistance-heating-wire-andresistance-wire/kanthal-a-1/.

Loyaika, S.K., et al., Poiseuille flow and thermal creep flow in 15 long, rectangular channels in the molecular and transition flow regimes, J. Vac. Sci. Technol., (1976) vol. 13, No. 6, 1188-1192.

Loyaika, S.K., et al., Thermal transpiration: A comparison of experiment and theory, J. Vac. Sci. Technol., (1978) vol. 15, No. 6, 1844-1152.

Mitragotri, S., et al., Overcoming the challenges in administering biopharmaceuticals: formulation and delivery strategies, Nature Reviews (2014) vol. 13, 655-672.

Siddiqui, N, et al., A study of viscosity, surface tension and volume flow rate of some edible and medicinal oils, International Journal of Science, Environment and Technology, vol. 2, No. 6 (2013) 1318-1326.

TEMCO Industrial. Electrical resistance information found on the internet at https://www.temcoindustrial.com/product-guides/wire-cable-and-accessories/resistance-andnon-resistance-wire/kanthal-wire.html.

(56) References Cited

OTHER PUBLICATIONS

Wang K., et al., A self-sustaining thermal transpiration gas pump and SOFC power generation system, Proceedings of the Combustion Institute 34 (2013) 3327-3334.
Xu, F., et al. "Adiabatic calorimetry and thermal analysis on acetaminophen." Journal of thermal analysis and calorimetry 83.1 (2005): 187-191.
Yamaguchi, Hiroki, et al. "Mass flow rate measurement of thermal creep flow from transitional to slip flow regime." Journal of Fluid Mechanics 795 (2016): 690-707.
Zhuravlev, E., et al., Fast scanning power compensated differential scanning nano-calorimetr: 1. The device, Thermochimica Acta 505 (2010) 1-13.
European Patent Office. Office Action for application 17738873.3. dated Sep. 17, 2020.
Woolley, C. et al. "Ereptiospiration." Bioengineering 4.2 (2017): 33.
Japan Patent Office. Notification of Reason for Refusal for application 2018-536100. dated Nov. 17, 2020. With translation. 7 pages.

* cited by examiner

EREPTIOSPIRATION DEVICE FOR MEDICINAL WAXES, SOLIDS, BIOPOLYMERS, OR HIGHLY VISCOUS OILS, AND CANNABINOIDS

CROSS-REFERENCE TO RELATED APPLICATIONS

This application represents the U.S. National Stage of International Application No. PCT/US2017/013046, filed Jan. 11, 2017, which claims the benefit of priority from U.S. Prov. Pat. App. Ser. No. 62/277,083, filed Jan. 11, 2016, under the same title and incorporated fully herein by reference.

BACKGROUND

Lung inhalation of airborne, aerosolized or vaporized medications is a means for drug delivery noted for fast action, non-invasiveness, and more patient compatibility as compared to injection, ingestion, and transdermal modes. Indication for inhalation delivery is desired especially for patients suffering from nausea or those requiring fast pain relief in settings where needle use is inconvenient or undesired.

A particularly important category of medications that are considered waxes and solid or highly viscous oils are the Cannabinoids such as Dronabinol, which is an FDA approved medication for nausea and pain, and Cannabidiol, which is currently being considered as an alternative to Dronabinol since it does not create psychotropic effects. These and similar Cannabinoids are currently ingested in a variety of ways, including inhalation, but no method or device for continuous ereptiospiration of the pure or mixtures of Cannabinoids without the use of solvents or through direct burning has been developed as prior art. Ereptiospiration is defined herein as the forcible thermal transfer to the air of solid, viscous, waxy, or highly viscous materials that would not vaporize through boiling or would degrade as a consequence of heating, melting, and/or boiling. To ereptiospirate the material—i.e., to forcibly and rapidly transfer the material from the viscous state to the vapor phase without thermal degradation of the material—the material is moved rapidly through a heating zone. Non-flow methods that rapidly vaporize materials such as practiced in the state of the art of ultra-fast, chip-based scanning calorimetry or thin film heaters are limited to very small quantities and cannot provide sustained delivery to the vapor phase, since they need to be recharged with new material. In contrast, an ereptiospiration device is flow-based and will deliver continuously into the vapor phase as long as the device has a sustained source of electrical power. In ereptiospiration, flow is created by establishing Knudsen or transitional Knudsen flow, which is a phenomena that has been widely observed and well understood to occur due to the presence of a pressure difference created by the temperature gradient generated by the electrical power and the relatively small pore or set of small porous channels where flow occurs.

SUMMARY

In a first aspect, provided herein is a device for ereptiospiration of an inhalable material. The device includes a heating member operatively positioned to provide heat to at least a portion of an inhalable material comprising a wax or solid, biopolymer, or highly viscous oil; a metallic fiber bundle in communication with the inhalable material and in communication with the heating member such that the metallic fiber bundle conducts heat from the heating member to the inhalable material; an electrical energy source capable of providing power to the heating member; and a mouthpiece connectable to the ereptiospiration chamber, wherein, upon receiving power from the electrical energy source, the heating member provides via the metallic fiber bundle heat above the ereptiospiration temperature of the wax or the solid or highly viscous oil of the inhalable material to release into the ambient air from the inhalable material. The mouthpiece can comprise an oral aspiration tube for transporting the vapor to a user's mouth in response to aspiration by the user's mouth. In some cases, the device further comprises a filter operatively positioned within the mouthpiece to remove particulates from vapor released from the inhalable material.

The device can continuously erepitiospirate the inhalable material. The inhalable material can comprise at least one extract of at least one plant, wherein the extract has not undergone an extraction or purification step to remove a substantial proportion of waxes or oil. The extract can comprise one or more cannabinoid selected from the group consisting of tetrahydrocannabinol (THC), Δ9-tetrahydrocannabinol, Δ9-tetrahydrocannabinol propyl analogue, cannabidiol (CBD), cannabidiol propyl analogue, cannabinol, cannabichromene, cannabichromene propyl analogue, and cannabigerol, or any mixture thereof.

The electrical energy source can be a portable battery. The electrical energy source can provide between about 3 and about 8 watts of power to the heating member. The electrical energy source can provide sufficient power to the heating member to ereptiospirate the inhalable medium at a rate of about 10 mg/minute to about 45 mg/minute. The metallic fiber bundle can comprise a metal such as Kanthal or Nichrome.

In another aspect, this disclosure provides a device for ereptiospirating an inhalable material, the device including at least: a heating member operatively positioned to provide heat to at least a portion of an inhalable material comprising a wax, biopolymer, or solid or highly viscous oil; a metallic fiber bundle in communication with the inhalable material and in communication with the heating member such that the metallic fiber bundle conducts heat from the heating member to the inhalable material; a circuit control panel that meters dosage and allows for the monitoring of usage; an electrical energy source capable of providing power to the heating member; and a mouthpiece connectable to the ereptiospiration chamber. Upon receiving power from the electrical energy source, the heating member provides via the metallic fiber bundle heat above the ereptiospiration temperature of the wax, biopolymer or solid or highly viscous oil of the inhalable material to release vapor from the inhalable material.

The mouthpiece may be an oral aspiration tube for transporting the inhalable material to a user's mouth in response to aspiration by the user's mouth. The device may further include a filter operatively positioned within the mouthpiece to remove particulates from vapor released from the inhalable material. The device may continuously ereptiospirate the inhalable material, which may include at least one extract of at least one plant, wherein the extract has not undergone an extraction or purification step to remove a substantial proportion of waxes or oil. The extract may include one or more cannabinoid selected from the group consisting of tetrahydrocannabinol (THC), Δ9-tetrahydrocannabinol, Δ9-tetrahydrocannabinol propyl analogue, cannabidiol (CBD), cannabidiol propyl analogue, cannabinol, cannabichromene, cannabichromene propyl analogue, and cannabigerol, or any mixture thereof. The inhalable material may include at least one biopolymer and/or at least one analgesic.

The electrical energy source may be a portable battery, and/or may provide between about 3 and about 8 watts of power to the heating member, and/or sufficient power to the heating member to ereptiospirate the inhalable medium at a rate of about 10 mg/minute to about 45 mg/minute. The metallic fiber bundle may be Kanthal or Nichrome.

In yet another aspect, the present disclosure provides a device for delivering an inhalable material to a user. The device includes at least: a sample chamber for containing the inhalable material in a viscous state, wherein in the viscous state the inhalable material is one of a wax, a biopolymer, a solid oil, and a highly viscous oil; an ereptiospiration chamber at least partially isolated from the sample chamber, and an ereptiospiration assembly operatively positioned to heat a portion of the inhalable material in the sample chamber to release vapor from the inhalable material into the ereptiospiration chamber, the user inhaling the vapor from the ereptiospiration chamber when using the device. The ereptiospiration assembly may include a heating member and a metallic fiber bundle in communication with the inhalable material and in communication with the heating member such that the metallic fiber bundle conducts heat from the heating member to the inhalable material. The device may further include a barrier isolating the ereptiospiration chamber from the sample chamber, the ereptiospiration assembly extending through the barrier; to heat the portion of the inhalable material in the sample chamber to release the vapor into the ereptiospiration chamber, the ereptiospiration assembly may heat the portion of the inhalable material in the viscous state to reduce viscosity of the portion until the portion flows from the sample chamber into the ereptiospiration chamber, and, when the portion is in the ereptiospiration chamber, heat the portion to release the vapor.

The ereptiospiration assembly may continuously ereptiospirate the inhalable material while the user is using the device. The inhalable material may include at least one extract of at least one plant, wherein the extract has not undergone an extraction or purification step to remove a substantial proportion of waxes or oil.

Other features and advantages of the present invention will be apparent from the following description taken in conjunction with the accompanying drawings, in which like reference characters designate the same of similar parts throughout the figures thereof.

DETAILED DESCRIPTION

This invention describes a cartridge that can be loaded with medical waxes, solid or highly viscous oils in order to continuously ereptiospirate and deliver dosages to patients via direct lung inhalation. The cartridge is battery powered for portability in order to provide medication when needed. Also, the mechanisms of local ereptiospiration, efficient heat integration, and passive control of the ereptiospiration process constitute new art in rapid drug delivery via inhalation of waxes, biopolymers, solid, or highly viscous oils without dilution or purification using solvents other than water. No prior art teaches a portable ereptiospirater system specially designed for medicinal waxes, biopolymers, and heavy oils that can provide controllable dosages from a single cartridge. The objective of this invention is to show that with the extension of a ereptiospiration system that can liquefy solids and moderate liquid viscosity leads to the delivery of medicinal waxes and oils via ereptiospiration.

In 1997, the National Institutes of Health issued a review of scientific literature concerning beneficial medicinal effects of marijuana. The NIH report recommended that researchers develop alternative dosage forms for the drug, such as a "smoke free" inhaled delivery system. The ereptiospiraters and other devices described herein are advantageous over those in the prior art that require extraction (such as solvent extraction) or other processes to remove waxy materials from cannabinoid-containing plant extracts. Whereas the presently described devices make advantageous use of waxy elements of crude plant extracts, waxes, wax esters, and other components of inert ballast material are generally considered to be "unwanted" elements that impede ereptiospirater-based delivery of cannabinoids or *cannabis* extracts. See, for example, U.S. Patent Application Serial No. 2015/0105455. With respect to the devices described herein, the integration of heat within the cartridge simplifies the overall design and creates a passive control system to initiate and moderate ereptiospiration at a sufficient level so that pure medicine can be delivered in a time efficient manner to quickly achieve therapeutic levels of cannabinoids without exposing patients to solvents or combustion products. In addition, the devices described herein can be used for rapid, solvent-free delivery of pure cannabinoids, including those cannabinoid derivatives that do not have psychotropic effects, for the treatment of or management of symptoms (e.g., nausea, pain) associated with cancer, brain disorders, and other chronic conditions.

Figure 1:
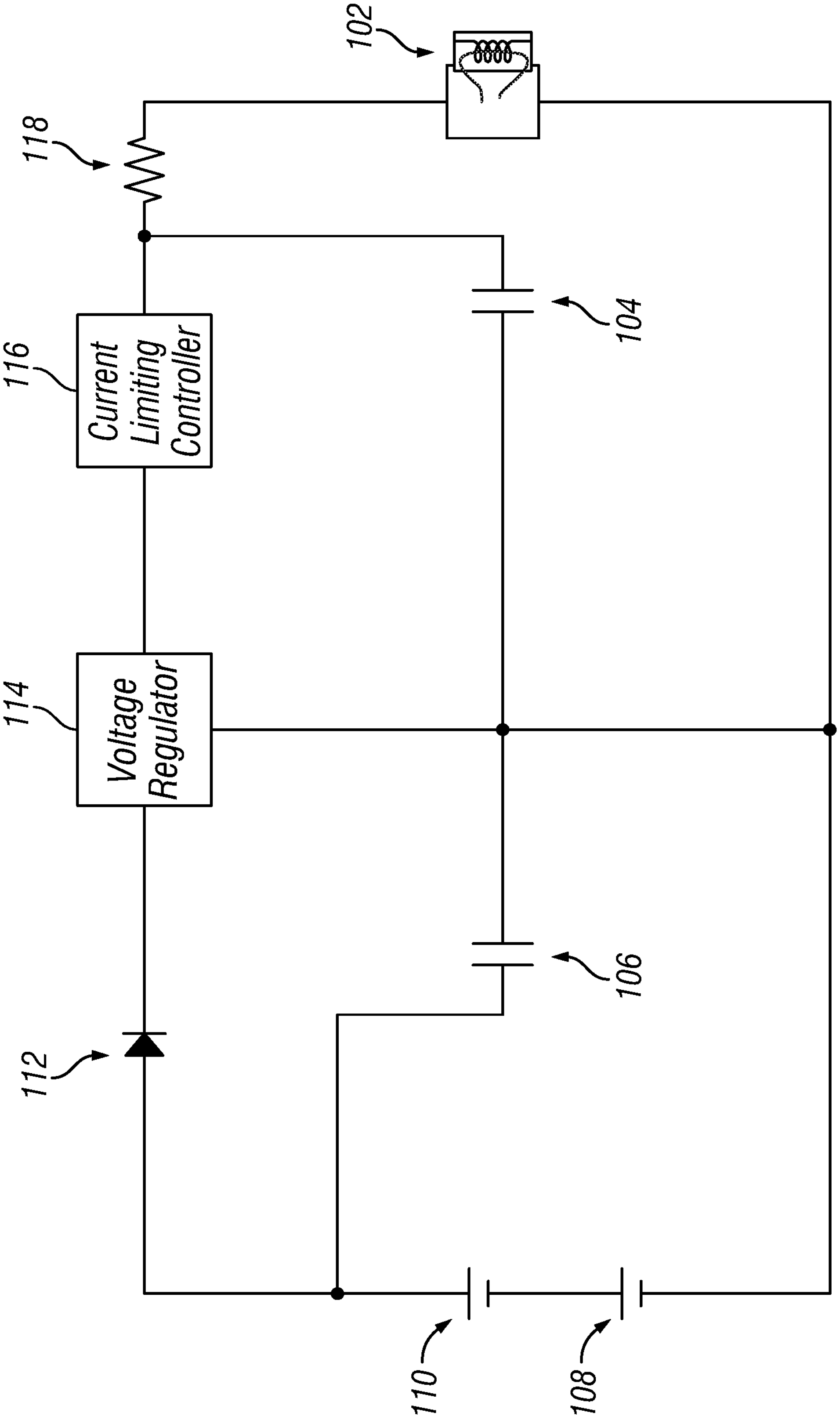
FIG. 1 is a circuit configuration diagram of an embodiment of a device for ereptiospirating an inhalable material.

Accordingly, provided herein is a ereptiospirater device comprising a cartridge. Referring to FIG. 1, power is supplied by rechargeable batteries 108 & 110, within a circuit with a voltage controller 114 and a current 116 controller that together provide constant potential and maintain current below a maximum current for safe operation. A coil and fiber bundle assembly 102 constitutes the electrical load of the circuit, with capacitors 104 & 106 added for additional stabilization of power and a diode 112 to ensure a positive direction for current flow.

Figure 2:
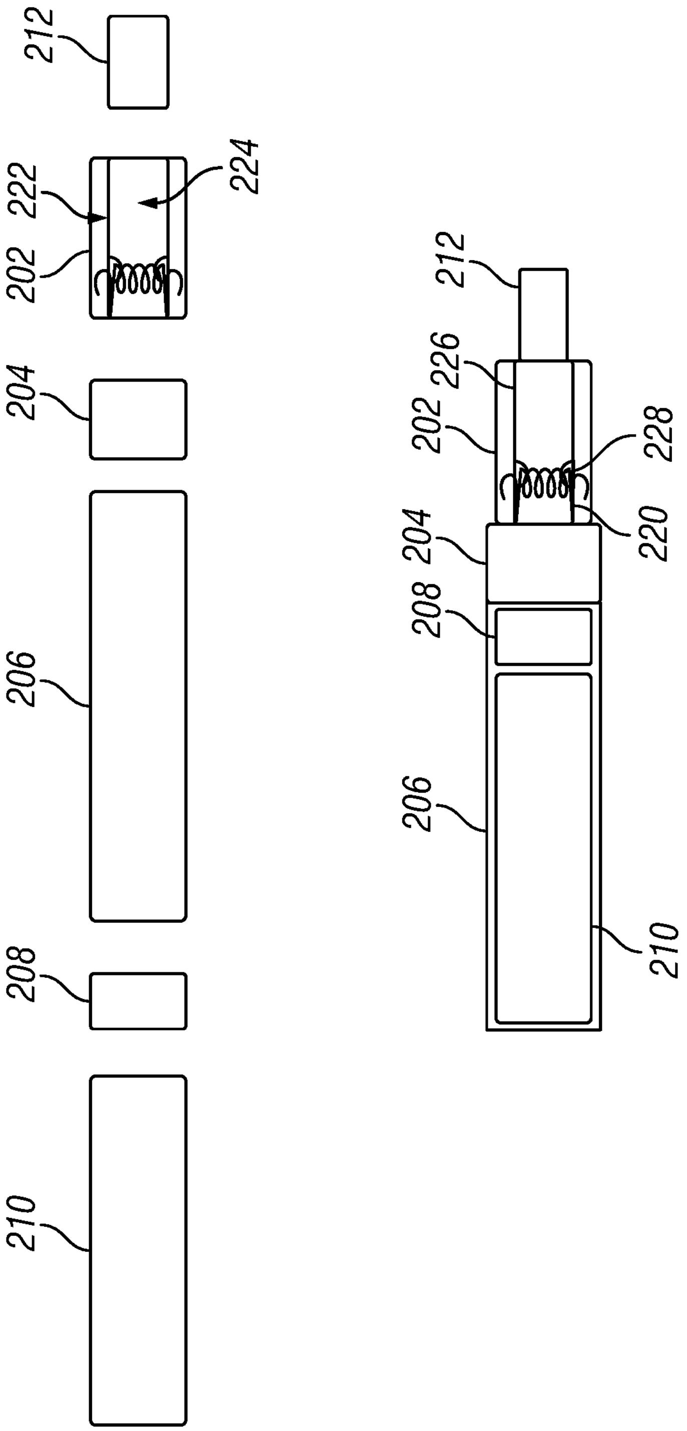
FIG. 2 is a schematic arrangement of an embodiment of a device for ereptiospirating an inhalable material.

FIG. 2 illustrates an exemplary device for ereptiospirating a sample of a material. A cartridge 202 comprises a chamber that is configured to isolate a wire coil 220 from a sample chamber 222 containing the supply of material to be ereptiospirated. For example, the wire coil 220 can be in an ereptiospiration chamber 224 that is separated from the sample chamber 222 by a barrier 226. In some cases, the wire coil 220 comprises nichrome or kanthal wire. In preferred embodiments, the ereptiospiration chamber 224 includes a small coil 220 wrapped around a metallic fiber bundle 228, where the metallic fiber bundle 228 is threaded through an opening in the barrier 226 and wrapped inside the sample chamber 222. The metallic fiber bundle 228 can be a metallic wool such as steel wool, aluminum wool, bronze wool, or any other metal fiber that can be aligned to provide channels to flow the inhalable material to the coil 220. As the medicinal wax or oil flows onto the fiber bundle 228, the fiber bundle 228 becomes coated with the inhalable material, which moderates the electrical resistivity of the metal used as the fiber bundle 228 material, increasing electrical resistance sufficiently in order to divert power to coil 220 heating. For example, the "unprimed" fiber bundle 228 may have a resistance of 5-10 ohms, while the primed fiber bundle 228 may have a resistance of about 3.4-4 ohms. In this manner, the metallic fiber bundle 228 provides a compatible surface for high temperature ereptiospiration of waxes and oils, and supports flow of hydrophobic medication. In addition, the fiber bundle 228 provides a thermally absorbing pad whereby heat from the ereptiospiration chamber 224 ensures a continuous supply of ereptiospiratable material from the sample chamber 222.

The sample chamber 222 is designed to hold a medicinal wax, biopolymer gel, hydrated biopolymer, or solid or highly viscous oil to be ereptiospirated. When in contact with the fiber bundle 228 or with an interior surface of the sample chamber 222, such as the interior surface formed by the barrier 226, the medicinal wax or oil composition is heated, whereby the wax melts and the viscosity of the oil is lowered. The remaining material flows downward (i.e., toward the end where the fiber bundle 228 is positioned) through the cartridge 202 during the period of heating as the cartridge 202 begins to empty. Inversion during storage or confinement of liquid below the fiber bundle 228 using a ledge (not shown) ensures that flow is maintained toward the fiber bundle 228 during subsequent uses. The barrier 226 between the sample chamber 222 and coil 220 is used to prevent excessive liquid flowing to the coil 220 due to gravity, which can create splattering and stop ereptiospiration due to the presence of a thick layer of material that needs to be removed or ereptiospirated before a more controlled and steady ereptiospiration of fiber bundle metered material can resume. To ensure that the device remains cool enough for the user to handle, an adaptor 204 having "fins" (openings that allow air flow) can be included to decrease the temperature experienced by the user when handling the device.

To load the cartridge 202, a medicinal wax or oil sample may, if needed, first be warmed to lower the sample viscosity. Concurrently, all or part of the interior of the cartridge may be chilled to a temperature where the material does not flow. This allows the heated sample to more easily adhere to the interior surfaces of the sample chamber 222 as the sample cools. When the sample is at a suitable viscosity, it may be applied to the chilled surface of the interior cartridge both on top of and below the fiber bundle, and onto the fiber bundle 228 up to 2 mm from where the coil 220 is wrapped around the fiber bundle 228. The cartridge 202 may be screwed or snapped into connection with the housing 206, creating a liquid tight seal.

When electrical power is supplied to the coil 220 at a constant voltage, the current is initially high until ereptiospiration commences after about 30 seconds, depending upon the melting point or flow point of the wax or oil. As used herein, the term "ereptiospiration" refers to the process of producing a vapor (gas phase) from a solid or liquid material, produced preferably by heating. Once ereptiospiration begins, the current drops to a level consistent with the increased resistance due to a film of the medication that is ereptiospirating at the coil 220 surface. Current is allowed to fluctuate with the priming and pumping actions of the coil 220 and fiber bundle 228 initially; as the sample chamber 222 empties, it reaches a steady temperature profile which also steadies the current. This mode of operation provides steady ereptiospiration after an initial priming period, sufficiently regulated for the intended purpose of steady flow, without the employment of an active control element.

As the sample chamber 222 is drained of medicinal wax or oil, the fiber bundle 228 will continue to meter the medication to the coil 220 until all of the material is ereptiospirated. Metering is dictated by the porosity of the fiber bundle 228, specifically the average pore size, and the amount of power available. After ereptiospiration is completed, the current increases to the level observed before the fiber bundle 228 was primed. The increase in current once all wax, solid, biopolymer, or oil is ereptiospirated in the sample chamber can be used as a signal to shut off power and replace the ereptiospiration unit with a new cartridge 202.

As used herein, the terms "medicinal wax" and "medicinal oil" refer to a waxy or solid or highly viscous oil compositions comprising a medication. A waxy composition can comprise a wax or wax ester of animal and vegetable origin. Plant waxes are particularly advantageous for the purposes of the present invention. Those which can preferably be used are cuticular waxes of lower and higher plants, algae, lichens, mosses and fungi, such as, for example, candelilla wax, carnauba wax, Japan wax, esparto grass wax, cork wax, rice wax, sugar cane wax, fruit waxes, e.g. apple wax, flower waxes, leaf waxes from conifers, coffee wax, flax wax, sesame wax, jojoba oil and the like. It will be understood that waxes that can be used according to the present invention are not limited to these examples. Further, the term "wax" is not intended to limit the invention to a component that is necessarily solid at room temperature.

In exemplary embodiments, a medicinal wax or oil comprises at least one extract from at least one *cannabis* plant. The *cannabis* plant(s) preferably include at least one cannabinoid. Crude *cannabis* plant extracts generally comprise cannabinoids, waxes, and long chain molecules (e.g., unsaturated fatty acids). The term "*Cannabis* plant(s)" encompasses wild type *Cannabis sativa* and also variants thereof, including *cannabis* chemovars which naturally contain different amounts of the individual cannabinoids, *Cannabis sativa* subspecies indica including the variants var. indica and var. kafiristanica, *Cannabis* indica and also plants which are the result of genetic crosses, self-crosses or hybrids thereof. The term "*Cannabis* plant material" is to be interpreted accordingly as encompassing plant material derived from one or more *cannabis* plants. For the avoidance of doubt it is hereby stated that "*cannabis* plant material" includes dried *cannabis* biomass.

Cannabinoids useful for the invention provided herein include any member of a group of substances that are structurally related to tetrahydrocannabinol (THC) and that bind to a cannabinoid receptor such as CB1 or CB2 or both. The cannabinoid can be a naturally occurring compound (e.g., present in *Cannabis*), a compound metabolized by a plant or animal, or a synthetic derivative. In some cases, the cannabinoid can be any of 9-tetrahydrocannabinol, 8-tetrahydrocannabinol, (+)-1,1-dimethylheptyl analog of 7-hydroxy delta-6-tetrahydrocannabinol, 3-(5'-cyano-1',1'-dimethylpentyl)-1-(4-N-morpholinobutyryloxy) delta 8-tetrahydrocannabinol hydrochloride], dexanabinol, nabilone, levonantradol, or N-(2-hydroxyethyl)hexadecanoamide. In other cases, cannabinoids of the present invention can be any of the non-psychotropic cannabinoid 3-dimethylnepty 11 carboxylic acid homologine 8, delta-8-tetrahydrocannabinol. See Burstein et al., *J. Med Chem.* 35:3135 (1992).

In some cases, the cannabinoid can be Delta-9-tetrahydrocannabinol, also known as Dronabinol. Dronabinol is naturally-occurring and has been extracted from *Cannabis sativa* L. (marijuana). It has also been produced chemically as described in U.S. Pat. No. 3,668,224. Dronabinol is a light-yellow resinous oil that is sticky at room temperature, but hardens upon refrigeration. It turns into a flowable liquid when heated at higher temperatures. Dronabinol is insoluble in water and typically formulated in sesame oil. It has a pKa of 10.6 and an octanol-water partition coefficient: 6,000:1 at pH 7. While Dronabinol is available in natural form (i.e., extracted from a plant), the cannabinoid can be synthesized using the following starting materials: olivetol (also known as 5-pentylresorcinol or 5-pentyl-1,3-benzenediol) and p-2, 8-menthadien-2-ol (PMD).

Ereptiospiration devices provided herein are useful for treatment of cannabinoid-sensitive disorders. As used herein, the term "cannabinoid-sensitive disorder" refers any disorder or condition that, when a cannabinoid or a cannabinoid receptor modulator is administered, modulates a pathophysiologic pathway that ameliorates the disorder or clinically relevant symptoms thereof. Relevant pathophysiologic pathways can be desirably modulated by present medicaments. For example, administration may modulate the pathways of acid (e.g., GABA, glutamate), monoamine (e.g., histamine, dopamine, serotonin, noradrenaline) purine (e.g., adenosine, ADP, ATP), peptide (e.g., somatostatin, neuropeptide Y, neurokinin, cholecystokinin), vanilloid, prostanoid, opioid and/or other neurotransmitters. Accordingly, cannabinoid-sensitive disorders include disorders mediated by or sensitive to neurotransmitter action. Examples of cannabinoid-sensitive disorders are sleep apnea, anxiety, stress, headache, nausea, glaucoma, pain, arthritis, irritable bowel syndrome, ulcerative colitis, Crohn's disease, anorexia or cachexia syndrome, bladder dysfunction, spasticity due to multiple sclerosis, Huntington's disease, and Alzheimer's disease.

The ereptiospiration devices provided herein use an electrically powered heating coil and metallic fiber bundle for heat integration. Preferably, the device comprises a heating member operatively positioned to provide heat to at least a portion of an inhalable material comprising a wax or solid or highly viscous oil; a metallic fiber bundle in communication with the inhalable material and in communication with the heating member such that the metallic delivers the inhalable material to the heating member, an electrical energy source (e.g., a rechargeable battery 210 connected to a recharging interface 208 such as a Universal Serial Bus (USB) port and interface, as shown in FIG. 2) capable of providing power to the heating member, whereby upon receiving power from the electrical energy source via the metallic fiber bundle the heating member provides heat above the ereptiospiration temperature of the wax or the solid or highly viscous oil of the inhalable material to release into ambient air from the inhalable material. This configuration eliminates the need for a separate heating chamber or an external energy source. In addition, this configuration requires less time to generate sufficient heat to melt waxes and solid oils or reducing the viscosity of viscous oils, thereby generating flow in the metallic fiber bundle, since less than the entire cartridge is heated. Other advantages of the configurations described herein include, without limitation, the following:

- Re-solidification or increase in viscosity due to coil power being turned off does not prevent restarting ereptiospiration afterwards by turning power on again.
- Heating via heat integration maintains device at safe temperatures for holding ereptiospirater, due to localization of high temperatures and fast cooling after power is shut off.
- Cannabinoids can be ereptiospirated using the device while maintaining physiologically relevant action.
- Material forcibly introduced into the air by the device is fine and dispersed, with an average temperature <85° F.
- Dosage rates of at least 10-30 mg/minute can be maintained using a portable, handheld battery as the electrical energy source.

In exemplary embodiments, the electrical resistance of the coil and metallic fiber bundle with the solid wax or oil medication provides a passive control element. Constant voltage operation of the device generates a feedback loop of resistance that is dictated by the level of medication at the coil surface and fiber bundle interior. Power to the coil is increased when priming or when the rate of metering of medicinal wax or oil at the coil is low, and decreases when the rate of metering is high. Flow of solid wax or oil through the fiber bundle increases the resistance which increases the load, thereby decreasing the power to the coil by lowering the current for a constant voltage system. Current monitoring can be used as an ereptiospiration rate sensor for initial priming and for automatic power shutoff when the cartridge is depleted of the medicinal wax or oil.

Referring again to FIG. 2, the device can additionally include a mouthpiece 212. In exemplary embodiments, the mouthpiece 212 is connectable to the ereptiospiration chamber 224. In some cases, the mouthpiece 212 comprises an oral aspiration tube for transporting the inhalable material to a user's mouth in response to aspiration by the user's mouth.

In exemplary embodiments, the device further includes a mouthpiece capable of receiving a filter (not shown). In some cases, a filter screen is adapted for placement over an opening of the mouthpiece, whereby the filter is within the mouthpiece. The filter screen can include a filter housing, and a filter mesh inside the filter housing. Preferably, the filter is made of a material that helps filter out undesirable components such as particulates in the vapor before it is inhaled by a user. Example filter materials include, without limitation, polyurethane foam, polyester, or activated carbon. The filter mesh may be a metal mesh, such as a stainless wire cloth. The mesh is preferably of a size to filter out large particles that might be in the vapor.

Figure 3:
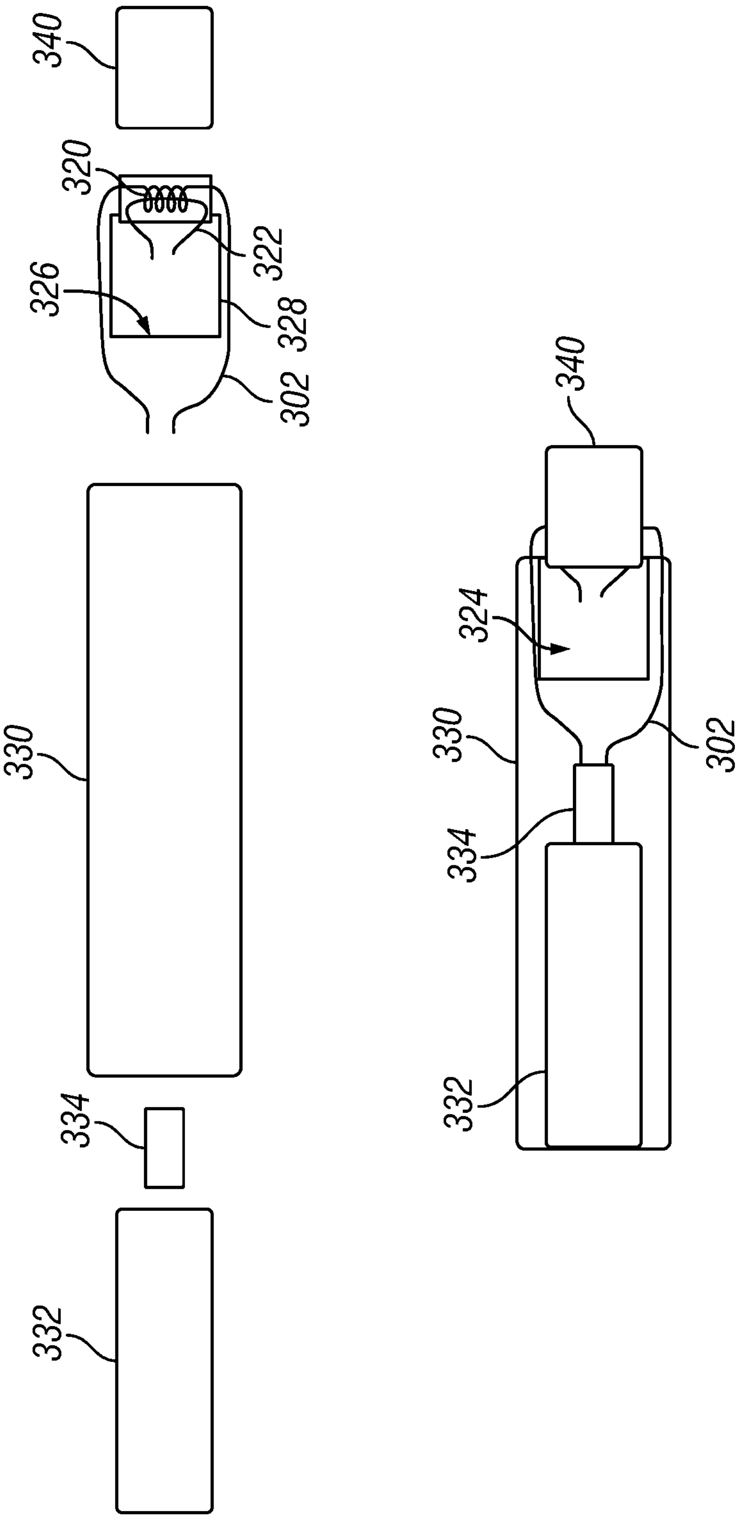
FIG. 3 is a schematic arrangement of an alternative embodiment of a device for ereptiospirating an inhalable material.

In some embodiments, the device has an alternative configuration as shown in FIG. 3. The alternative configuration of FIG. 3 achieves the same goals as the device shown in FIG. 2. In the alternative configuration, the cartridge 302 housing the fiber bundle 322 and coil 320 can be rectangular. For heat integration controlled by the power to the coil 320, a thin reflective aluminum plate 326 is used to line the sample chamber 324 where the fiber bundle 322 is tightly wrapped, and an insulated housing 328 defines the sample chamber 324. The insulation of the housing 328 warms the sample chamber 324 to maintain a sufficient temperature to have freely flowing medication through the fiber bundle 322. A mouthpiece 340 may attach to the cartridge to facilitate withdrawal of the vapor as described above. The cartridge 302 may attach to a proximal end of a main housing 330 that encloses and protects the sample chamber 324 and also contains a power source 332. In some cases, a microcontroller 334 is provided to serve as a switch, for example implementing the circuitry shown in FIG. 1. The microcontroller 334 regulates delivery of power to the cartridge 302. The microcontroller 334 can further measure the resistance of the fiber bundle 322 during ereptiospiration and translate the information, based on calibration data, into a dosage rate. In some embodiments, the microcontroller 334 may be housed near the fiber bundle 322, and may switch power off to the cartridge 302 when the time and dosage rate meet a set point value stored by the microcontroller 334. A control circuit including the microcontroller 334 can further include a connection to the power source 332 for power, MOSFET switch, and Bluetooth, USB, or other interfacing capability for receiving input data to set operation parameters, such as readjusting setpoint.

EXAMPLES

Example 1—Device with Stainless Steel Fiber Bundle to Ereptiospirate Coconut Wax Metallic wool is aligned and twisted to form a fiber bundle. A typical size fiber bundle for the intended application of loading a 2-3 gram cartridge with wax or highly viscous or solid oil has a diameter of 0.6 mm and a length of 65 mm (35 mm for a cartridge with approximately 250 mg of sample).

Use of a new fiber bundle requires an initial priming period of 30 seconds to 1 15 minute. After the priming of the fiber bundle, coconut wax can be ereptiospirated at an average rate of 30 mg/min (trials range from 15-45 mg/min) when approximately 250 mg is used as a sample. The resistance over the trials was observed to be between 2-4 ohms (Ω), with an optimal value around 3.5 ohms. Current ranged from 1-1.9 amperes (A) depending on the age of the fiber bundle. The air temperature near the coil is between 185° C.-233° C., with temperatures in the sample reservoir at 55° C.

Example 2—Device with Stainless Steel Fiber Bundle to Ereptiospirate Beeswax Use of a new fiber bundle requires a longer priming period, between 90 seconds and 2 minutes. After the priming period the ereptiospiration rate is consistent between 2-4 mg/min. Resistance is comparable to coconut wax, between 3.4-4 ohms. The current is observed to be between 1-1.9 A (higher during fiber bundle priming).

Example 3—Device with Stainless Steel Fiber Bundle to Ereptiospirate Dronabinol Use of a new fiber bundle requires an initial priming period of 45 seconds to 1 minute. After the priming of the fiber bundle, Dronabinol can be ereptiospirated at an average rate of 22 mg/min (trials range from 12-25 mg/min) when approximately 350 mg is used as a sample. Current ranged from 1-1.8 A depending on the age of the fiber bundle. The temperature in the sample reservoir was found to be 58° C.

Example 4—Device with Stainless Steel Fiber Bundle to Ereptiospirate White Petrolatum Use of a new fiber bundle requires a very short priming period (15-30 seconds), after which the material may be ereptiospirated at a rate between 19-50 mg/min with an average rate of 30 mg/min. The current ranged from 1-1.9 A depending on the age of the fiber bundle (approximately 1.89 A with an unprimed fiber bundle, and between 1.2-1.4 A when stable ereptiospiration is observed. Resistance measurements were similar to those observed for other ereptiospirated materials (between 3-4Ω) with an optimal resistance around 3.5Ω.

Example 5—Device with Stainless Steel Fiber Bundle does not Ereptiospirate Palm Wax Palm wax was tested and not observed to ereptiospirate using the current system. With a melting point around 85° C., no liquid was produced in the cartridge and was not able to prime the fiber bundle. It would be possible to melt and ereptiospirate this material using a battery with a higher current limit that would allow fiber bundle temperatures to increase such that the sample reservoir may reach temperatures high enough to melt the palm wax. However, heating the fiber bundle to these temperatures could pose a number of safety and user experience problems. This example teaches the need for liquid creation in order to flow material into the fiber bundle for ereptiospiration by the coil.

Example 6—Device with Stainless Steel Fiber Bundle to Ereptiospirate Lard

A cartridge was filled with lard. After a short priming period (30-60 seconds) the material was ereptiospirated at a rate between 4-13 mg/min. The current ranged from 1-1.65 Amps, depending upon the age of the fiber bundle.

Example 7—Device with Stainless Steel Fiber Bundle does not Ereptiospirate Soy Wax Soy wax was tested and not observed to prime the fiber bundle using the current system. With a melting point around 75° C., no liquid was produced in the cartridge under the current heating conditions and the fiber bundle could not be primed. Using a fiber bundle that was pre-primed with coconut wax, ereptiospiration of the soy wax was observed at a rate between 15-35 mg/min. The current during these trials using a pre-primed fiber bundle was observed to be between 0.9-1.2 A, with a resistance similar to that observed for the ereptiospiration of other materials. Continued ereptiospiration of the wax after the material immediately in contact with the fiber bundle was not observed, as melting of the soy wax did not occur in the cartridge and it did not flow onto the fiber bundle to replace used material. It is possible to melt and produce continuous ereptiospiration of soy wax with a battery allowing a higher current limit, although the temperatures required may be undesirable and could produce safety problems. This example, in addition to that for palm wax, teaches the importance of material flow into the fiber bundle for continuous ereptiospiration.

Example 8—Steel Wool Fiber Bundle to Ereptiospirate Lanolin

Lanolin was placed in glass reservoirs and the fiber bundle was lowered into the sample. Alternatively, the fiber bundle was coiled and sandwiched in lanolin between two glass slides. After fiber bundle priming, ereptiospiration was observed at a rate of between 6-16 mg/min, with higher rates associated with the coiled fiber bundle. The current ranged from 1.1-1.7 A.

Example 9—Use of a Articulate Air Filter

In another embodiment, a particular air filter was used with a stainless steel fiber bundle to, upon ereptiospiration of coconut oil, remove particulates from vapor released from the inhalable material.

Example 10, Device with Cylindrical Cartridge and Stainless Steel Fiber Bundle to Ereptiospirate Coconut Oil Use of a new fiber bundle requires an initial priming period of approximately 30 seconds. During the priming period the current is observed to be higher (around 1.8 A). After the fiber bundle is primed the current drops to 1.4-1.6 A, and ereptiospiration is observed at a rate of 6-12 mg/min with a resistance of 1.8-3.0Ω.

Example 11. Device with Cylindrical Cartridge and Stainless Steel Fiber Bundle to Ereptiospirate THC-A Use of a new fiber bundle requires a 5-10 second initial priming period. After the priming of the fiber bundle, THC-A can be ereptiospirated at an average rate of 6 mg/min over a sustained period (trials range from 5-25 mg/min depending on the amount of material available). When approximately 250 mg is loaded into the cartridge, and proper storing of the cartridge occurs between trials, 6 mg/min ereptiospiration is observed until there is less than 100 mg remaining. Resistance of the cartridge was found to range from 2.0-3.4Ω and the temperature of the outside of the cartridge was found to be 28 C. Ereptiospirated material was compared to the original substance using GC-MS and FTIR to ensure degradation did not take place during sample delivery.

Figure 4:
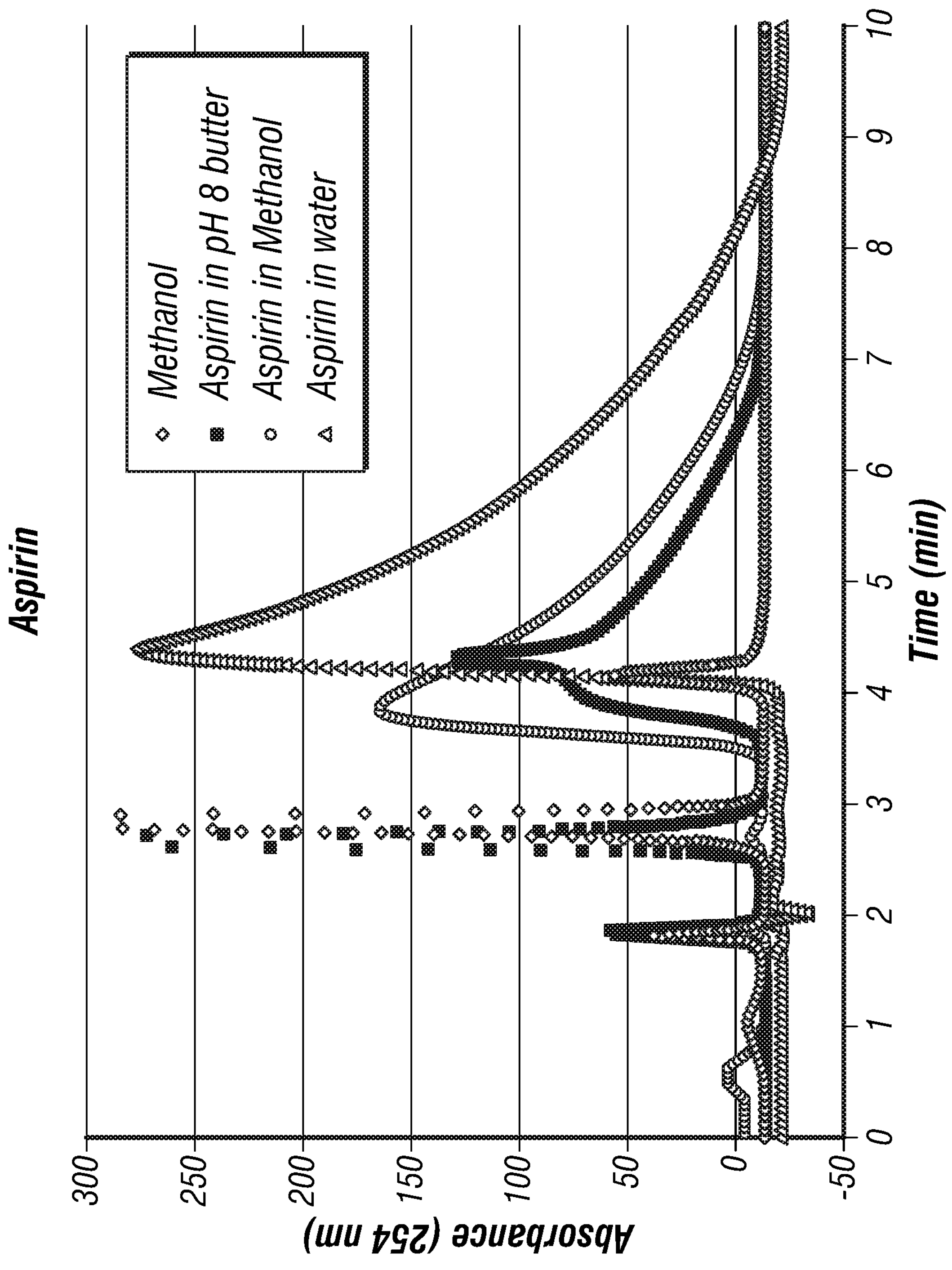
FIG. 4 is a plot diagram of experimental results of ereptiospirating acetylsalicylic acid using a device in accordance with the present disclosure.

Example 12. Stainless Steel Wool Fiber Bundle to Ereptiospirate Acetylsalicylic Acid Acetylsalicylic acid was placed in a 10 ml glass beaker and melted. The fiber bundle was lowered into the sample so the ends were submerged. After an initial priming period of 10-20 seconds ereptiospiration was observed at a rate of 1-2 mg/min. The current ranged from 1.5-1.8 A. Ereptiospirated material was collected from three separate experiments and compared to the original powdered substance using HPLC testing. HPLC testing was performed using an isocratic elution using a 50:50 ratio of water to methanol at a rate of 1 mL/min on a C18 column. Chromatography results indicate the presence of acetylsalicylic acid in the inhaled material without evidence of degradation (FIG. 4). Due to column overloading and interactions with the column materials, the retention times for acetylsalicylic acid shift during use.

Example 13. Stainless Steel Wool Fiber Bundle to Ereptiospirate Ibuprofen

Figure 5:
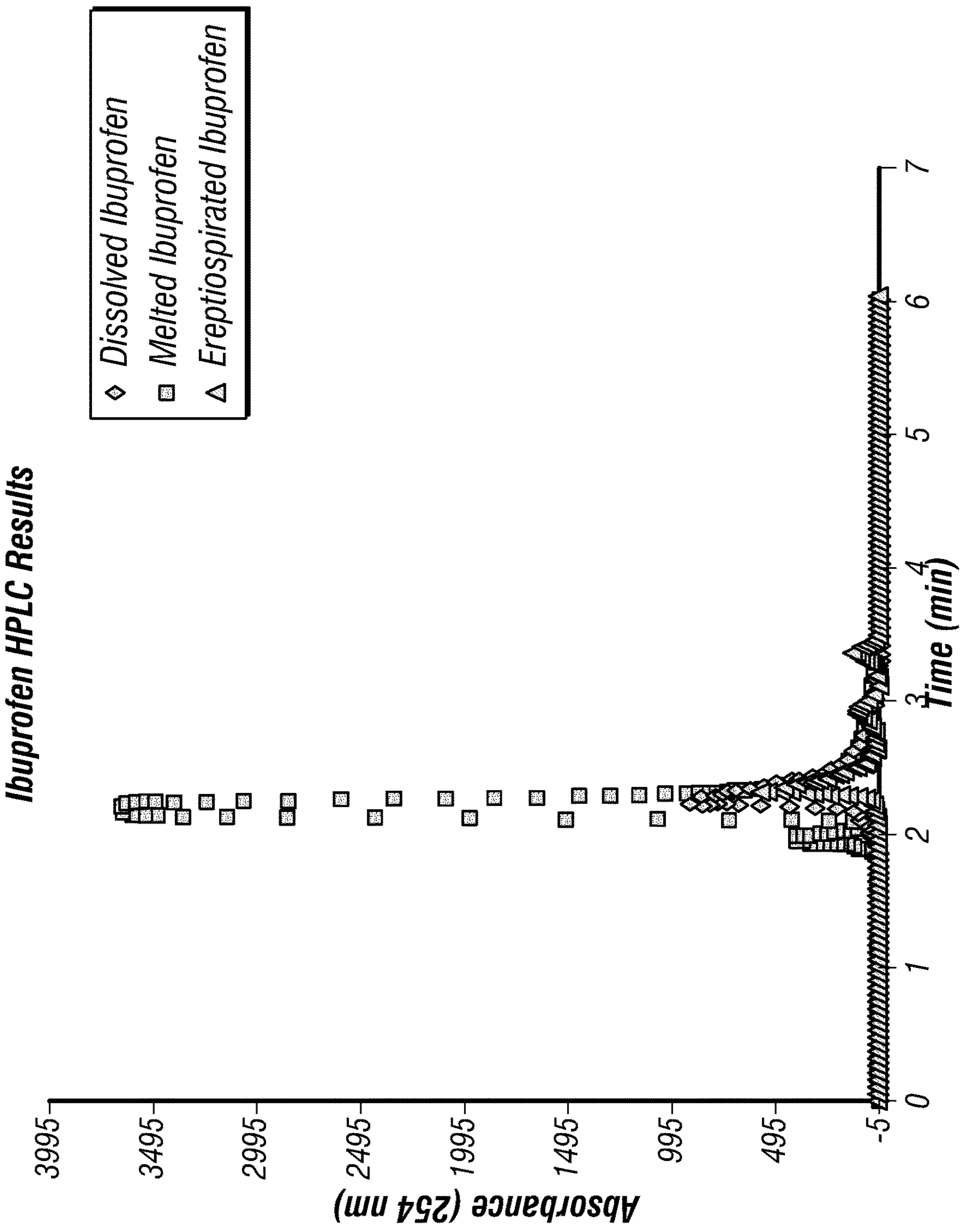
FIG. 5 is a plot diagram of experimental results of ereptiospirating ibuprofen using a device in accordance with the present disclosure.

Ibuprofen was placed in a 10 ml beaker and melted. A fiber bundle was placed in the sample such that the ends were submerged. After an initial priming period of 5-10 seconds ereptiospiration was observed between 1-3 mg/min. The current ranged from 1.4-1.9 A. Ereptiospirated material was collected from three separate experiments and compared to the original powdered and melted substance using HPLC testing. HPLC testing was performed using an isocratic elution in 100% methanol at a flow rate of 1 mL/min on a C18 column. Results indicate the presence of ibuprofen in the inhaled material. The primary peak evident in the ereptiospirated material was consistent with that observed in the powdered and melted ibuprofen samples (FIG. 5).

Figure 6:
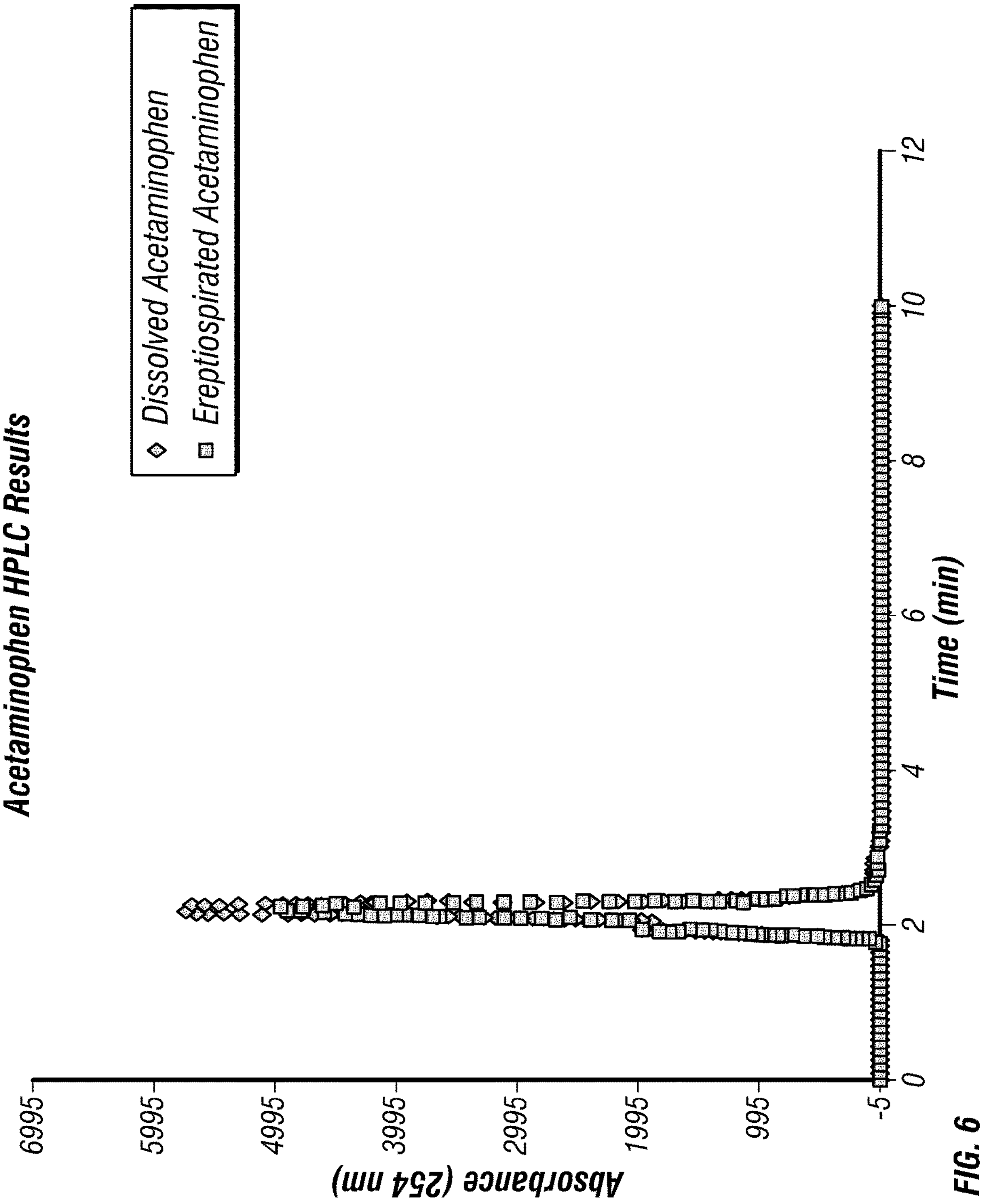
FIG. 6 is a plot diagram of experimental results of ereptiospirating acetaminophen using a device in accordance with the present disclosure.

Example 14. Stainless Steel Wool Fiber Bundle to Ereptiospirate Acetaminophen Acetaminophen was placed in a 10 ml beaker and melted. The fiber bundle was placed into the sample in such a way that the ends were submerged. After an initial priming period of 10-20 seconds ereptiospiration was observed at a rate of 1-2 mg/min. The current ranged from 1.6-1.9 A. Ereptiospirated material was collected from three separate experiments and compared to the original powdered substance using HPLC testing. HPLC testing was performed using an isocratic elution using a 50:50 ratio of water to methanol at a rate of 1 mL/min on a C18 column. Results indicate the presence of acetylsalicylic acid in the inhaled material without evidence of degradation (FIG. 6).

Example 15. Device with Cylindrical Cartridge and Stainless Steel Fiber Bundle to Ereptiospirate Bovine Gelatin A ten percent gel of gelatin in DI water was produced by dissolving gelatin powder in water, heating the solution to 100 C, and then cooling it to 4 C. The cylindrical cartridge was filled with 300-350 mg of gelatin and allowed to ereptiospirate for 5 minutes at a rate of 0.5-3 mg/min. Material was collected and dissolved in PBS buffer. This ereptiospirated material was evaluated by digestion with pepsin followed by SDS-PAGE and quantified using the Bradford assay. To perform pepsin digestion, modifications were made to a method developed for the differentiation of porcine and bovine gelatin. Briefly, three samples of ereptiospirated gelatin (200 μL each) and three samples of gelatin starting material (500 μL each) were mixed with approximately 100 mg of a pepsin tablet in 1.7 mL Eppendorf tubes. Starting material was melted prior to the addition of pepsin to aid in mixing. Samples were incubated at 60 C for 1, 2, and 3 hours. Following incubation samples were neutralized and centrifuged for 3 minutes. The pellet formed after centrifuging was mixed with 20 μL of 5% SDS solution and heated to 85 C in a water bath for 5 minutes. Following this samples were centrifuged a second time for 3 minutes and supernatant was mixed with SDS-PAGE sample running buffer (0.5 M Tris-HCl, pH 6.8 with 4% SDS and 20% glycerol). Samples were loaded onto a 10% gel and subjected to electrophoresis at a constant voltage of 120 V for 4 hours. After coomassie staining, imaging shows that the gelatin could be ereptiospirated using the device. SDS-PAGE results show the hydrolyzed gelatin evident in all three digest samples. The polypeptide concentration increased proportionately with the time of the digest. The Bradford assay was performed using both gelatin starting material and ereptiospirated samples. Briefly, gelatin samples diluted in PBS to produce 100 μL standards ranging from 0-1 mg. Samples were heated and added to disposable plastic cuvettes with 1 mL of Bradford reagent. UV-Vis spectra were captured in triplicate to form a standard curve. By comparing the curve to the spectra of the standard gelatin and ereptiospirated samples, it was found that ereptiospirated material was present in a lower concentration than gelatin before ereptiospiration (489 μg compared with 759 μg from the same volume sample).

Example 16. Device with Cylindrical Cartridge and Stainless Steel Fiber Bundle does not Ereptiospirate Bovine Serum Albumin Bovine serum albumin (BSA) was mixed with gelatin to a concentration of 1 mg/mL. The cylindrical cartridge was filled with 300-350 mg of the gelatin/BSA mixture (approximately 300-350 μg of BSA present). While the cartridge was able to prime, ereptiospiration of the BSA was not observed. A thick, gelatinous layer was left surrounding the fiber bundle on the interior of the cartridge and there was no evidence of BSA in the ereptiospirated material.

Example 17. Device with Cylindrical Cartridge and Stainless Steel Fiber Bundle to Ereptiospirate Genomic Onion DNA Genomic DNA was extracted from white onion and purified through washing with TE buffer (10 mM Tris pH 8.0 with 1 mM Ethylenediaminetetraacetic acid). Briefly, two onions were blended with ½ cup of DI water. The puree was placed in a clean container and cup liquid hand soap was added and gently mixed in. After a five minute incubation at room temperature, the solution was strained through paper towels to remove the solid onion material. Chilled 90% isopropyl alcohol was added in a 1:1 ratio to the strained liquid. Precipitated DNA was centrifuged and washed 3× with TE buffer to purify the samples. The cylindrical cartridge was loaded with approximately 300 mg of purified DNA material and allowed to ereptiospirate for 5 minutes at a rate of 0.5-3 mg/min. Ereptiospirated material was collected from the cartridge. RAPD PCR (random amplification of polymorphic DNA polymerase chain reaction) was performed in duplicate on ereptiospirated material, original DNA, negative controls missing onion DNA or dNTPs, and a positive control of calf thymus. RAPD PCR is a well-studied method for the simple amplification of DNA. Despite its simple and reliable operation, several studies have noted that there are a variety of experimental parameters that can influence the outcome.[2-5] Optimization of these parameters is necessary to prevent false bands from appearing in electrophoresis, or non-reproducible results.[2,3] One study, applying RAPD PCR to the study of Cuban Triatominae, focused on the effects of changing experimental parameters to determine optimal RAPD PCR conditions to achieve reproducible results. This optimized protocol was used to perform the RAPD PCR. Following 40 rounds of PCR amplification, the samples were subjected to electrophoresis in a 1% agarose gel. After running at 80 V for 4 hours the gel was developed overnight with an ethidium bromide solution and imaged to observe PCR product. Gel images indicate that genomic DNA was present in the ereptiospirated material as well as in the starting onion DNA material.

We claim:

1. A device for ereptiospirating an inhalable material comprising a sample chamber including an inhalable material comprising a wax, biopolymer, or solid or viscous oil;

an ereptiospiration chamber at least partially isolated from the sample chamber;

a heating member operatively positioned to provide heat to at least a portion of the inhalable material;

a metallic fiber bundle in communication with the inhalable material and in communication with the heating member such that the metallic fiber bundle conducts heat from the heating member to the inhalable material;

a circuit control panel that meters dosage and allows for the monitoring of usage;

an electrical energy source capable of providing power to the heating member;

a mouthpiece connectable to the ereptiospiration chamber, and a barrier isolating the ereptiospiration chamber from the sample chamber, wherein the metallic fiber bundle is threaded through an opening in the barrier and wrapped inside the sample chamber;

wherein, upon receiving power from the electrical energy source, the heating member provides via the metallic fiber bundle heat above the ereptiospiration temperature of the wax, biopolymer, or solid or viscous oil thereby melting or reducing the viscosity of the inhalable material to cause a portion of the inhalable material to flow from the sample chamber into the ereptiospiration chamber and releasing a vapor comprising ereptiospirated inhalable material in the ereptiospiration chamber.

2. The device of claim 1, wherein the mouthpiece comprises an oral aspiration tube for transporting the inhalable material to a user's mouth in response to aspiration by the user's mouth.

3. The device of claim 1, further comprising a filter operatively positioned within the mouthpiece to remove particulates from vapor released from the inhalable material.

4. The device of claim 1, wherein the device continuously ereptiospirates the inhalable material.

5. The device of claim 1, wherein the inhalable material comprises at least one extract of at least one plant, and wherein the extract has not undergone an extraction or purification step to remove a substantial proportion of wax or oil.

6. The device of claim 5, wherein the extract comprises one or more cannabinoid selected from the group consisting of tetrahydrocannabinol (THC), Δ9-tetrahydrocannabmol, Δ9-tetrahydrocannabinol propyl analogue, cannabidiol (CBD), cannabidiol propyl analogue, cannabinol, cannabichromene, cannabichromene propyl analogue, and cannabigerol, or any mixture thereof.

7. The device of claim 1, wherein the electrical energy source is a portable battery.

8. The device of claim 1, wherein the electrical energy source provides between 2 and 14 watts of power to the heating member.

9. The device of claim 1, whereby the electrical energy source provides sufficient power to the heating member to ereptiospirate the inhalable material at a rate of 10 mg/minute to 45 mg/minute.

10. The device of claim 1, wherein the metallic fiber bundle comprises stainless steel.

11. The device of claim 1, wherein the inhalable material comprises at least one biopolymer.

12. The device of claim 1, wherein the inhalable material comprises at least one analgesic.

13. The device of claim 1, wherein the heating member comprises stainless steel, a NiCr alloy, or a FeCrAl alloy.

* * * * *